(12) United States Patent
Fabian et al.

(10) Patent No.: US 10,915,863 B2
(45) Date of Patent: Feb. 9, 2021

(54) MANAGING MEDICAL EXAMINATIONS IN A POPULATION

(71) Applicant: Medial Research Ltd., Kfar-Malal (IL)

(72) Inventors: Offer Fabian, Moshav Zur Moshe (IL); Ori Geva, Hod-HaSharon (IL)

(73) Assignee: Medial Research Ltd., Kfar-Malal (IL)

( * ) Notice: Subject to any disclaimer, the term of this patent is extended or adjusted under 35 U.S.C. 154(b) by 989 days.

(21) Appl. No.: 14/900,189

(22) PCT Filed: Jun. 19, 2014

(86) PCT No.: PCT/IL2014/050558
§ 371 (c)(1),
(2) Date: Dec. 21, 2015

(87) PCT Pub. No.: WO2014/203258
PCT Pub. Date: Dec. 24, 2014

(65) Prior Publication Data
US 2016/0180049 A1 Jun. 23, 2016

Related U.S. Application Data

(60) Provisional application No. 61/836,687, filed on Jun. 19, 2013.

(51) Int. Cl.
*G16H 50/70* (2018.01)
*G06Q 10/10* (2012.01)
(Continued)

(52) U.S. Cl.
CPC .............. *G06Q 10/10* (2013.01); *G16H 10/60* (2018.01); *G16H 50/30* (2018.01)

(58) Field of Classification Search
USPC ........................................................ 705/2–4
See application file for complete search history.

(56) References Cited

U.S. PATENT DOCUMENTS 6,059,724 A 5/2000 Campell et al.
8,010,295 B1 * 8/2011 Magness ............... G06F 19/363
435/4
(Continued)

FOREIGN PATENT DOCUMENTS

WO WO 2014/203258 12/2014

OTHER PUBLICATIONS

Palmer C, Duan X, Hawley S, Scholler N, Thorpe JD, Sahota RA, et al. (2008) Systematic Evaluation of Candidate Blood Markers for Detecting Ovarian Cancer. PLoS ONE 3(7): e2633. https://doi.org/10.1371/journal.pone.0002633.*
(Continued)

*Primary Examiner* — Mark Holcomb

(57) ABSTRACT

A method of managing an allocation of medical examinations. The method comprises documenting, in at least one dataset, for each one of a plurality of individuals of a certain population, a plurality of historical medical test results, calculating, using a computerized processor, a plurality of relative scores each indicative of a risk of having a medical condition for one of the plurality of individuals based on respective the plurality of historical medical test results, each one of the plurality of relative scores is relative to the other of the plurality of relative scores, providing a population examination framework defining at least one criterion for selecting an individual, from the plurality of individuals, for a diagnosis of the medical condition, selecting a subgroup of the plurality of individuals according to the population examination framework, and designating members of the subgroup to perform the medical examinations.

17 Claims, 2 Drawing Sheets

(51) Int. Cl.
*G16H 10/60* (2018.01)
*G16H 50/30* (2018.01)

(56) References Cited

U.S. PATENT DOCUMENTS

| | | | |
|---|---|---|---|
| 8,041,584 B2 | 10/2011 | Wu et al. | |
| 2002/0087276 A1 | 7/2002 | Otvos | |
| 2003/0187688 A1* | 10/2003 | Fey | G06Q 50/22 |
| | | | 705/2 |
| 2008/0133267 A1* | 6/2008 | Maltezos | G06Q 50/22 |
| | | | 705/2 |
| 2008/0171916 A1 | 7/2008 | Feder et al. | |
| 2008/0255879 A1* | 10/2008 | Baumel | G16H 40/20 |
| | | | 705/2 |
| 2010/0100392 A1* | 4/2010 | Rothman | G16H 15/00 |
| | | | 705/2 |
| 2010/0198648 A1 | 8/2010 | Bank et al. | |
| 2011/0082712 A1* | 4/2011 | Eberhardt, III | G06Q 10/10 |
| | | | 705/4 |
| 2011/0106556 A1* | 5/2011 | Patel | G06F 19/3456 |
| | | | 705/2 |
| 2012/0303381 A1* | 11/2012 | Bessette | A61B 5/743 |
| | | | 705/2 |
| 2013/0035951 A1* | 2/2013 | Frey | G06F 19/3481 |
| | | | 705/2 |
| 2013/0144642 A1* | 6/2013 | Bessette | G06Q 10/10 |
| | | | 705/2 |
| 2014/0074509 A1* | 3/2014 | Amarasingham | G06F 19/00 |
| | | | 705/3 |

OTHER PUBLICATIONS

International Preliminary Report on Patentability dated Dec. 30, 2015 From the International Bureau of WIPO Re. Application No. PCT/IL2014/050558.

International Search Report and the Written Opinion dated Oct. 2, 2014 From the International Searching Authority Re. Application No. PCT/IL2014/050558.

Requisition by the Examiner dated May 26, 2020 From the Innovation, Science and Economic Development Canada, Canadian Intellectual Property Office Re. Application No. 2,950,728. (8 Pages).

* cited by examiner

MANAGING MEDICAL EXAMINATIONS IN A POPULATION

RELATED APPLICATIONS

This application is a National Phase of PCT Patent Application No. PCT/IL2014/050558 having International filing date of Jun. 19, 2014, which claims the benefit of priority under 35 USC § 119(e) of U.S. Provisional Patent Application No. 61/836,687 filed on Jun. 19, 2013. The contents of the above applications are all incorporated by reference as if fully set forth herein in their entirety.

BACKGROUND

The present invention, in some embodiments thereof, relates to medical condition evaluation (including assessment or investigation) and, more particularly, but not exclusively, to methods and systems of managing allocation of medical examinations.

Due to the increasing complexity and cost of providing health care, there is an increasing emphasis on managing the health care process. The process extends from an individual presenting a health concern to a health care provider and continues through diagnosis, therapeutic selection, resource selection, treatment, and follow-up.

Efforts to manage health care included manual-historical systems where individual files recording actual treatment provided are usually manually reviewed to collect statistics on general categories of care or to review the appropriateness of treatment in a given case. Such methods are labor-intensive and inefficient. Efforts have been made to standardize data collection forms, descriptions of conditions, descriptions of treatment, and treatments in order to more efficiently collect and evaluate health care data. Other efforts have been made to automate the analysis of historical health care data for persons with particular health care conditions. These efforts focus mainly on collecting financial data and serve accounting and administrative functions.

SUMMARY

According to some embodiments of the present invention, there is provided a method of managing an allocation of medical examinations. The method comprises documenting, in at least one dataset, for each one of a plurality of individuals of a certain population, a plurality of historical medical test results, calculating, using a computerized processor, a plurality of relative scores each indicative of a risk of having a medical condition for one of the plurality of individuals based on respective the plurality of historical medical test results, each one of the plurality of relative scores is relative to the other of the plurality of relative scores, providing a population examination framework defining at least one criterion for selecting an individual, from the plurality of individuals, for an evaluation of the medical condition, selecting a subgroup of the plurality of individuals according to the population examination framework, and designating members of the subgroup to perform the medical examinations.

Optionally, the population examination framework defines a criterion defining a relative risk score threshold; wherein the selecting is performed according to the relative risk score threshold.

Optionally, the population examination framework defines a criterion defining a function; wherein the selecting is performed according to the function.

Optionally, the population examination framework defines an amount; wherein the selecting is performed such that the members of the subgroup are individuals with the highest relative scores among the plurality of individuals and such that the size of the subgroup matches the amount.

Optionally, the documenting comprises documenting at least one demographic parameter for each one of the plurality of individuals and selecting a member of the subgroup based on a respective the at least one demographic parameter.

Optionally, the plurality of historical medical test results comprises a plurality of blood test results.

Optionally, the plurality of historical medical test results comprises a plurality of urine test results.

Optionally, the plurality of historical medical test results comprises a plurality of physical evaluation test results.

Optionally, determining comprises receiving a budget for performing the medical examinations and calculating the amount based on the budget.

Optionally, the method further comprises updating, for each of at least some of the plurality of individuals, at least one new medical test result, recalculating the plurality of relative scores while taking into account a combination of the at least one new medical test result, respective the plurality of historical medical test results, and selecting an additional subgroup of the plurality of individuals based on the plurality of recalculated relative scores.

Optionally, the method further comprises documenting a plurality of outcomes of the medical examinations, recalculating the plurality of relative scores for one of the plurality of individuals based on respective the plurality of historical medical test results and respective the outcome, and selecting an additional subgroup of the plurality of individuals based on the plurality of recalculated relative scores.

According to some embodiments of the present invention, there is provided a system of managing an allocation of medical examinations. The system comprises at least one dataset which stores, for each one of a plurality of individuals of a certain population, a plurality of historical medical test results, a computerized processor, a non transitory memory which stores instructions for calculating, using a computerized processor, a plurality of relative scores each indicative of a risk of having a medical condition for one of the plurality of individuals based on respective the plurality of historical medical test results, each one of the plurality of relative scores is relative to the other of the plurality of relative scores, and selecting a subgroup of the plurality of individuals according to a population examination framework defining at least one criterion for selecting an individual, from the plurality of individuals, for an evaluation of the medical condition, and an output interface which designates members of the subgroup to perform the medical examinations.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
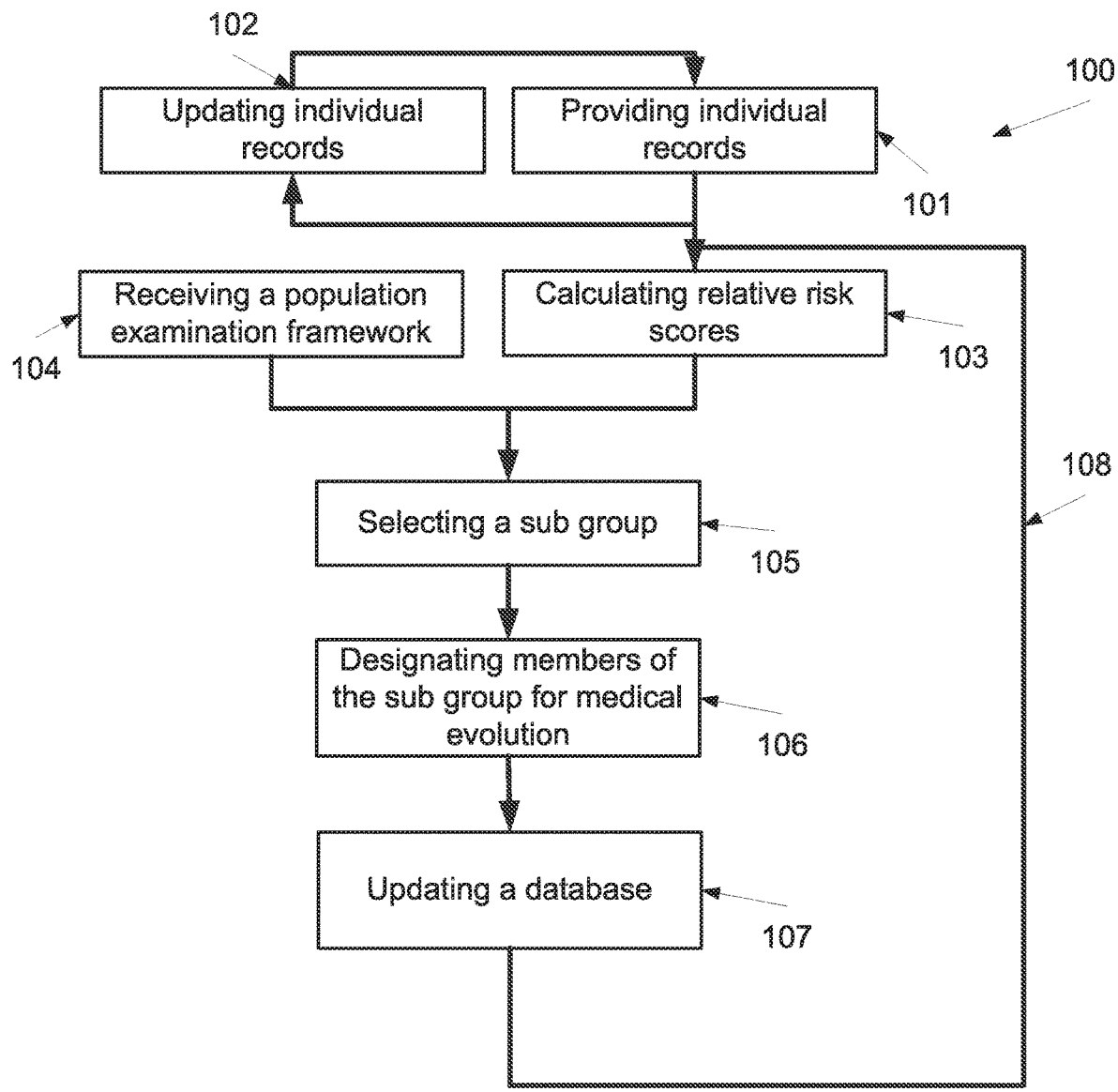
FIG. 1 is a flowchart of a method of managing an allocation of medical examinations to a group selected from a certain population of individuals based on dynamic and relative pathological risk classification of the individuals, according to some embodiments of the present invention.

The present invention, in some embodiments thereof, relates to medical condition evaluation and, more particularly, but not exclusively, to methods and systems of managing allocation of medical examinations.

According to an aspect of some embodiments of the present invention there are provided methods and systems for designating (e.g. periodically and/or upon demand) a subgroup of individuals from a certain population (e.g. insurants of one or more insurance companies) for a medical examination for a medical condition, for instance cancer screening. The subgroup is selected based on relative risk scores each calculated for another of the individuals. Optionally, the subgroup is selected according to a population examination framework, for example one or more criterions for selecting an individual, from the population, for an evaluation of the medical condition. Optionally, the population examination framework defines a given budget and/or a maximum number of medical examinations, for brevity also referred to as a budget. The relative risk score of each individual is calculated by one or more classifiers and based on an analysis of at least historical medical test results of the individuals, for example historical blood test results, historical urine test results, historical physical checkup results. In such methods and systems, individuals are dynamically selected for medical evaluation(s) based on up-to-date medical test data so that in any given time individuals which meet the population examination framework, for example having the highest risk of having the medical condition, are designated for medical evolution, such as cancer screening, regardless of changes in the budget (always the individuals at the highest risk are sent) and not only based on their demographic characteristics, for example gender and/or age.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Reference is now made to FIG. 1, which is a flowchart of a method 100 of managing an allocation of medical examinations and/or treatments to a group selected from a certain population of individuals based on dynamic and relative pathological risk classification of the individuals, according to some embodiments of the present invention. As used herein, a pathological risk may be an estimation of the chances of an individual to have a medical condition, such as diabetes, congestive heart failure, kidney failure and cancer, for example gastrointestinal cancer such as colon, stomach, rectum, or esophagus cancer. Other medical conditions may be pre-pathological conditions, such as pre-diabetic sugar blood level and pre congestive heart failure (CHF).

For brevity, the term medical condition includes medical conditions. As used herein, an allocation of a medical evaluation and/or treatment may be an allocation of a kit for self medical evaluation to an individual, an allocation of an appointment for a diagnosis by a physician or any other medical care provider, for example to diagnose cancer, for instance a colonoscopy session, an endoscopy session, and low dose computed tomography (LDCT) session, a preventive treatment and/or the like.

Figure 2:
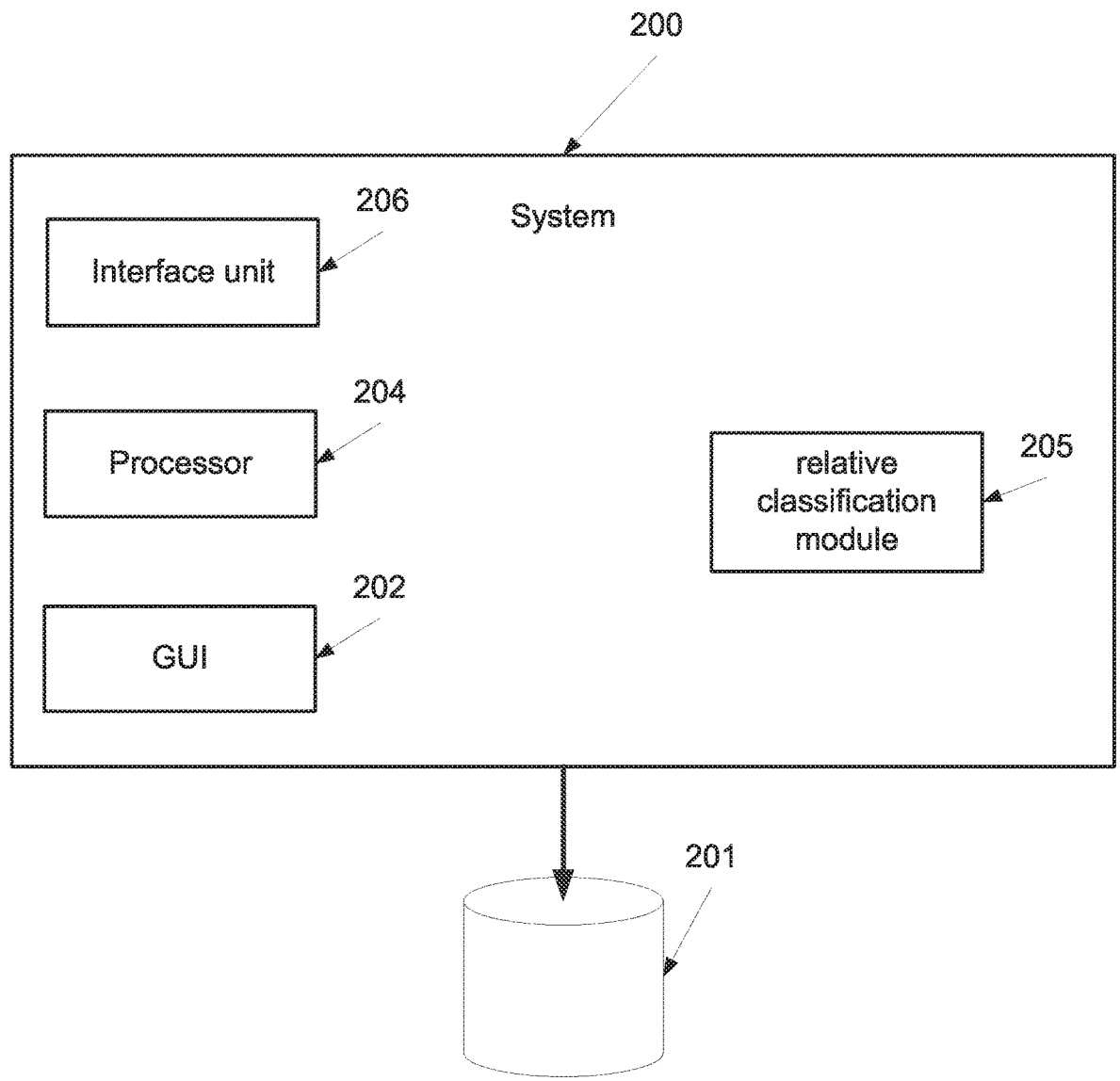
FIG. 2 is a schematic illustration of a system for an allocation of medical examinations based on dynamic classification, for example by implementing the method depicted in FIG. 1, according to some embodiments of the present invention.

Reference is also made to FIG. 2, which is a schematic illustration of a system 200 for an allocation of medical examinations and/or treatments based on dynamic classification, optionally iterative, for example by implementing the method depicted in FIG. 1, according to some embodiments of the present invention.

The system 200 includes to one or more medical record database(s) 201 and/or connected to a medical record database interface. The database(s) 201 include a plurality of individual records, also referred to as a plurality of individual samples, which describe, for each of another of a plurality of sampled individuals, one or more sets of a plurality of historical test results each set of another individual, and optionally one or more demographic parameter (s) and optionally one or more medical condition prognoses. As used herein, a demographic parameter includes age, gender, race, weight, national origin, geographical region of residence and/or the like. Optionally, a medical condition prognosis and/or indication is a binary indication. For example, for cancer, the medical condition prognosis and/or indication set according to a cancer registry record. Each individual record may also include diagnoses given by physicians in the past, historical measures, such as vital signs, hospitalization data and/or the like.

Optionally, the system 200 derives data from existing electronic health records (EHR) which include laboratory results (e.g. CBC, urine, glucose etc.), doctor visit data and observations, prescriptions, medications, demographic parameters and/or the like.

The individual records may be stored in a common sample record and/or gathered from (or accessed in) a number of independent and/or connected databases. Optionally, different data fields are extracted for different medical conditions. For example, blood test records may be used for scoring a risk level of a certain individual to have a medical condition such as cancer in relation to other individuals in the population and glucose and/or urinary test records may be used for scoring a risk level of the certain individual to have another medical condition such as diabetes in relation to other individuals in the population.

The different test results may be of commonly performed medical tests and/or medical tests held during the same period. Optionally, some sets of a plurality of historical test results have missing medical test results. These results are optionally completed by weighted averaging of the available medical test results of other individuals.

The system 200 further includes a processor 204, a relative classification module 205, and an interface unit 206, such as a network interface.

First, as shown at 101, a plurality of records each of one of a plurality of individuals of a certain population is provided. The certain population may be a plurality of insurants of one or more insurance companies, a plurality of individuals registered in a fund, a plurality of citizens of a country, a plurality of workers of a company and/or the like. The population may be a generally healthy population or a subset thereof. For example, the population may be individuals in the age of above 40 or between 50 and 75. Another example is a population at high risk group to start dialysis, for example with a kidney disease prognosis and/or indication.

As described above, data pertaining to different individuals may be registered in different individual records. The individual records data may be stored in existing databases or in a database of the system 100.

Optionally, as shown at 102, the database may be continuously updated with new medical test results, for instance an update of individual record(s) by blood test laboratories. The medical test results may be historical blood test results, historical urine test results, glucose levels, and/or historical physical checkup results Blood test results may be blood count outcomes and/or at least some of the following blood test results: red blood cells (RBC); white blood cell count—WBC (CBC); mean platelet volume (MPV); hemoglobin (HGB); hematocrit (HCT); mean cell volume (MCV); mean cell hemoglobin (MCH); mean corpuscular hemoglobin concentration (MCHC); red cell distribution width (RDW); platelet count (CBC); eosinophils count; neutrophils percentage; monocytes percentage; eosinophils percentage; basophils percentage; neutrophils count; monocytes count; and Platelets hematocrit (PCT).

Now, as shown at 103, the relative risk score is calculated for each one of the individuals in the population and/or for each one of the individuals in the population which has been found suitable for the medical examination, for example based on their demographic characteristics and/or their respective medical condition prognosis and/or indication. The relative risk score of a certain individual is indicative of the risk level of the certain individual in relation to other individuals in the population. The risk level is optionally calculated is two stages. First, a personal risk is evaluated using one or more classifier(s) that classify the risk(s) that the individual has one or more medical conditions based on an analysis of her respective one or more historical medical test result(s) and one or more demographic parameter(s).

Optionally, the personal risk is evaluated by one or more classifiers for risk evaluation which are generated based on analysis of a dataset of historical medical test results of a plurality of sampled individuals. The classifiers may be K-Nearest neighbors (KNN) classifiers, random forest classifiers, weighted linear regression classifiers and others. For example, the classifiers are as defined in PCT/IL2013/050368 filed May 2, 2013, which is incorporated herein by reference. Then, after a personal risk is calculated for each one of the individuals, a relative risk score is calculated for each one of the individuals. For example, the relative score is by ordering the individual based on their personal ranks and/or additional ordering characteristics.

Optionally, as shown at 104, a population examination framework is received. The population examination framework defines one or more criterions for selecting an individual, from the population, for an evaluation of the medical condition. The criterions may be having a relative risk score above a threshold and/or a relative risk score complying with certain function. For example, individuals with relative risk scores at selected risk score percentile(s), for instance the top 5%, 10%, 15%, and/or individuals with relative risk scores higher than a reference value, for example 5 times the relative risk scores average.

The criterion may be having a relative risk score higher than the risk score of any non selected individual. Such a criterion defines an amount of medical examinations to diagnose the medical condition(s) which may be performed in the certain population during a certain period. Optionally, the criterion is set by a budget allocated for performing a plurality of medical examinations to diagnose the medical condition(s) in the certain population. Such a budget may be translated to a number of medical examinations, for example based on the price of a medical examination. In such embodiments X individuals with the highest relative risk score are selected where X is a derivative of the budget. The criterion is being among the X individuals with the highest relative risk score.

Exemplary medical examinations are cancer screening, such as a gastrointestinal cancer examination, for instance, Breast cancer, Cervical cancer, Bowel cancer, Prostate cancer, Lung Cancer, skin cancer, and oral cavity cancer, routine screening is not recommended for bladder cancer, testicular cancer, ovarian cancer, and pancreatic cancer. The population examination framework may be defined manually and/or or received and/or extracted automatically. For example, the population examination framework is a yearly, monthly, and/or weekly budget which is allocated dynamically by an insurance company and/or a health organization.

Now, as shown at 105, a subgroup of the plurality of individuals is selected based on the relative scores where the number of members of the subgroup is optionally determined by the population examination framework, for example the calculated number of medical examinations. For instance, the subgroup includes the individuals who received the highest relative risk scores. Optionally, the population examination framework defines resources availability, for example a number of available colonoscopy slots for the next month and/or year. Optionally, the population examination framework defines a number of medical examinations which are allocated to a certain demographic group in the certain population and/or a set of budget portions each allocated to a different demographic and/or risk group in the population. A risk group may be defined by a personal risk threshold or range, one or more different demographic parameter(s) and/or a function or equation wherein the personal risk is substituted for example for checking if the personal risk value is more or less than X times the average of personal risks in the certain population.

This relative risk score is used to treat and/or diagnose and/or assess and/or review the high risk portion of the population. The definition of "high risk" (e.g. one that merits further testing/evaluation) may be done based on risk (e.g. top 10% or X5 average and up), resources (e.g. 5,000 colonoscopies in the coming quarter) and/or the like.

As shown at 106, this allows designating members of the subgroup to perform the medical examinations. The designation may include sending notifications to physicians, sending notifications to the members, updating a medical system and/or the like.

Optionally, as shown at 107, the database is updated with the outcomes of the medical examinations. For example, the medical condition prognosis and/or indication field in each of the respective plurality of individual records (the records of individuals going through the medical examinations) is updated. In such a manner, individuals may be selected in the next iteration based on a combination of factors that takes into account one or more previous medical condition prognoses.

As shown at 108, the process depicted in 101-107 is iteratively repeated so that a new subgroup is selected, for example periodically, for instance every few months and/or weeks and/or years, based on up-to-date data.

The above methods and systems may be set to periodically generate a new subgroup, for example based on a weekly population examination framework, a monthly population examination framework, and/or a yearly population examination framework.

The methods as described above are used in the fabrication of integrated circuit chips.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant methods and systems will be developed and the scope of the term a unit, a network, a database, and a processor is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel parameters of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a plurality of patients by managing an allocation of medical examinations, comprising:

documenting, in at least one dataset, for each one of a plurality of individuals of a certain population, a plurality of historical medical test results including a plurality of blood test results, and a plurality of outcomes of medical examinations;

generating, a combination of at least 10 blood test features based on said plurality of blood test results, each one of said at least 10 different blood test features is based on a blood test value of one of said plurality of blood test results; wherein each of said plurality blood test results comprises results of at least one of the following blood tests: red blood cells (RBC), hemoglobin (HGB), and hematocrit (HCT) and at least one result of the following blood tests hemoglobin (MCH) and mean corpuscular hemoglobin concentration (MCHC);

calculating, using a computerized processor, a plurality of relative scores each indicative of a risk of having a target medical condition which is evaluated by a target screening medical examination for one of said plurality of individuals based on respective said plurality of historical medical test results, said combination of at least 10 blood test features, and said plurality of outcomes of said medical examinations, each one of said plurality of relative scores is relative to the other of said plurality of relative scores; ranking the plurality of individuals according to respective relative risk scores;

providing a population examination framework defining a maximum number of the target screening medical examination for a time interval, and at least one criterion for selecting an individual, from said plurality of individuals, for an evaluation of said target medical condition using said target screening medical examination, wherein said at least one criterion defines a relative risk score above a threshold and/or a relative risk score complying with a certain function;

selecting a subgroup of said plurality of individuals with highest relative risk scores among said plurality of individuals meeting said at least one criterion and wherein the size of said subgroup matches said maximum number of target screening medical examinations according to said population examination framework;

designating members of said subgroup matching the maximum number of target screening medical examinations to perform said maximal number of target screening medical examinations, wherein said members of said subgroup are treated according to said outcome of said target screening medical examinations; and wherein the medical examination is cancer screening and the medical condition is cancer, and wherein the cancer screening is selected from the group consisting of: colonoscopy session, an endoscopy session, and low dose computed tomography (LDCT) session.

2. The method of claim 1, wherein said population examination framework define a criterion defining a relative risk score threshold; wherein said selecting is performed according to said relative risk score threshold.

3. The method of claim 1, wherein said population examination framework defines a criterion defining a function; wherein said selecting is performed according to said function.

4. The method of claim 1, wherein said documenting comprises documenting at least one demographic parameter for each one of said plurality of individuals and selecting a member of said subgroup based on a respective said at least one demographic parameter.

5. The method of claim 1, wherein said plurality of historical medical test results comprises a plurality of urine test results.

6. The method of claim 1, wherein said plurality of historical medical test results comprises a plurality of physical diagnosis test results.

7. The method of claim 1, wherein determining comprises receiving a budget for performing said medical examinations and calculating said amount based on said budget.

8. A system of treating a plurality of patients by managing an allocation of medical examinations, comprising:
at least one dataset which stores, for each one of a plurality of individuals of a certain population, a plurality of historical medical test results including a plurality of blood test results, and a plurality of outcomes of medical examinations;
a computerized processor; a non-transitory memory which stores instructions for:
generating, a combination of at least 10 blood test features based on said plurality of blood test results, each one of said at least 10 different blood test features is based on a blood test value of one of said plurality of blood test results;
wherein each of said plurality blood test results comprises results of at least one of the following blood tests: red blood cells (RBC), hemoglobin (HGB), and hematocrit (HCT) and at least one result of the following blood tests hemoglobin (MCH) and mean corpuscular hemoglobin concentration (MCHC);
calculating, using said computerized processor, a plurality of relative scores each indicative of a risk of having a target medical condition which is evaluated by a target screening medical examination for one of said plurality of individuals based on respective said plurality of historical medical test results, said combination of at least 10 blood test features, and said plurality of outcomes of said medical examinations, each one of said plurality of relative scores is relative to the other of said plurality of relative scores;
ranking the plurality of individuals according to respective relative risk scores;
selecting a subgroup of said plurality of individuals with highest relative risk scores among said plurality of individuals meeting said at least one criterion and wherein the size of said subgroup matches said maximum number of target screening medical examinations according to a population examination framework defining a maximum number of the target screening medical examination for a time interval, and at least one criterion for selecting an individual, from said plurality of individuals, for an evaluation of said target medical condition using said target screening medical examination, wherein said at least one criterion defines a relative risk score above a threshold and/or a relative risk score complying with a certain function;
an output interface which designates members of said subgroup matching the maximum number of target screening medical examinations to perform said maximal number of target screening medical examinations, wherein said members of said subgroup are treated according to said outcome of said target screening medical examinations; and
wherein the medical examination is cancer screening and the medical condition is cancer, and wherein the cancer screening is selected from the group consisting of: colonoscopy session, an endoscopy session, and low dose computed tomography (LDCT) session.

9. A computer program product for treating a plurality of patient by managing an allocation of medical examinations, comprising:
a non-transitory memory storing thereon code for execution by at least one hardware process, the code including instructions for:
documenting, in at least one dataset, for each one of a plurality of individuals of a certain population, a plurality of historical medical test results including a plurality of blood test results, and a plurality of outcomes of medical examinations;
generating, a combination of at least 10 blood test features based on said plurality of blood test results, each one of said at least 10 different blood test features is based on a blood test value of one of said plurality of blood test results;
wherein each of said plurality blood test results comprises results of at least one of the following blood tests: red blood cells (RBC), hemoglobin (HGB), and hematocrit (HCT) and at least one result of the following blood tests hemoglobin (MCH) and mean corpuscular hemoglobin concentration (MCHC);
calculating, using a computerized processor, a plurality of relative scores each indicative of a risk of having a target medical condition which is evaluated by a target screening medical examination for one of said plurality of individuals based on respective said plurality of historical medical test results, said combination of at least 10 blood test features, and said plurality of outcomes of said medical examinations, each one of said plurality of relative scores is relative to the other of said plurality of relative scores;
ranking the plurality of individuals according to respective relative risk scores; providing a population examination framework defining a maximum number of the target screening medical examination for a time interval, and at least one criterion for selecting an individual, from said plurality of individuals, for an evaluation of said target medical condition using said target screening medical examination, wherein said at least one criterion defines a relative risk score above a threshold and/or a relative risk score complying with a certain function;

selecting a subgroup of said plurality of individuals with highest relative risk scores among said plurality of individuals meeting said at least one criterion and wherein the size of said subgroup matches said maximum number of target screening medical examinations according to said population examination framework; and designating members of said subgroup matching the maximum number of target screening medical examinations to perform said maximal number of target screening medical examinations, wherein said members of said subgroup are treated according to said outcome of said target screening medical examinations; and wherein the medical examination is cancer screening and the medical condition is cancer, and wherein the cancer screening is selected from the group consisting of: colonoscopy session, an endoscopy session, and low dose computed tomography (LDCT) session.

10. The method of claim 1, wherein the cancer is selected from the group consisting of: Gastrointestinal cancer, Breast cancer, Cervical cancer, Bowel cancer, Prostate cancer, Lung Cancer, skin cancer, and oral cavity cancer.

11. The method of claim 1, further comprising computing a personal risk for each one of the plurality of individuals using a classifier that is fed at least a combination of a plurality of different blood test features based on the plurality of blood test results, the plurality of outcomes of medical examinations, and at least one demographic parameter, and the plurality of relative scores are computed by ordering the personal risk scores for the plurality of individuals.

12. The method of claim 1, wherein each of said plurality of blood test results individually have insufficient statistical significance correlating between the respective blood test result and risk of having the medical condition.

13. The method of claim 1, wherein the combination of at least 10 blood test features comprises between 10 and 20 blood test results.

14. The method of claim 1, wherein the combination of at least 10 blood test features based on said plurality of blood test results comprises results of at least one the following blood tests: white blood cell count - WBC (CBC); mean platelet volume (MPV); mean cell; platelet count (CBC); eosinophils count; neutrophils percentage; monocytes percentage; eosinophils percentage; basophils percentage; neutrophils count; monocytes count, red cell distribution width (RDW), Platelet hematocrit (PCT), and mean cell volume (MCV).

15. The method of claim 1, further comprising: updating, for each of at least some of said plurality of individuals, at least one new medical test result; recalculating said plurality of relative scores while taking into account the combination of at least 10 blood test features and including said at least one new medical test result; and selecting an additional subgroup of said plurality of individuals based on said plurality of recalculated relative scores.

16. The method of claim 1, further comprising: documenting a plurality of outcomes of said medical examinations; recalculating said plurality of relative scores for one of said plurality of individuals based on respective combination of at least 10 blood test features and including respective said outcome; and selecting an additional subgroup of said plurality of individuals based on said plurality of recalculated relative scores.

17. The method of claim 1, further comprising: updating the at least one dataset with an outcome of said target screening medical examination for computation of another relative risk score for selection of another subgroup for another maximum number of the target screening medical examinations for another time interval.

* * * * *